(12) United States Patent
Kobayashi et al.

(10) Patent No.: US 8,652,313 B2
(45) Date of Patent: Feb. 18, 2014

(54) ION SELECTIVE ELECTRODE CARTRIDGE

(75) Inventors: Teruyuki Kobayashi, Ibaraki (JP);
Tsuyoshi Uchida, Tokyo (JP)

(73) Assignee: Hitachi Chemical Company, Ltd.,
Tokyo (JP)

( * ) Notice: Subject to any disclaimer, the term of this patent is extended or adjusted under 35 U.S.C. 154(b) by 0 days.

(21) Appl. No.: 13/496,570

(22) PCT Filed: Sep. 17, 2010

(86) PCT No.: PCT/JP2010/066197
§ 371 (c)(1),
(2), (4) Date: Mar. 16, 2012

(87) PCT Pub. No.: WO2011/034168
PCT Pub. Date: Mar. 24, 2011

(65) Prior Publication Data
US 2012/0175253 A1 Jul. 12, 2012

(30) Foreign Application Priority Data

Sep. 18, 2009 (JP) ................. 2009-217505

(51) Int. Cl.
*G01N 27/333* (2006.01)
(52) U.S. Cl.
USPC ........................................ 204/411; 204/416
(58) Field of Classification Search
USPC ............ 204/416, 272, 670, 403.02, 411, 412;
429/94; 427/77
See application file for complete search history.

(56) References Cited

U.S. PATENT DOCUMENTS

| 3,574,079 | A | | 4/1971 | Kalman |
| 4,797,192 | A | | 1/1989 | Takiguchi |
| 5,580,441 | A | * | 12/1996 | Amemiya et al. ............ 205/789 |
| 6,096,275 | A | * | 8/2000 | Greenberg ................. 422/82.02 |
| 6,409,909 | B1 | * | 6/2002 | Spichiger-Keller et al. ......................... 205/777.5 |
| 2002/0033335 | A1 | | 3/2002 | Terashima et al. |
| 2008/0135409 | A1 | | 6/2008 | Sakuraoka et al. |

FOREIGN PATENT DOCUMENTS

| EP | 0 102 042 | 3/1984 |
| EP | 0 126 426 | 11/1984 |
| EP | 0 394 990 | 10/1990 |
| JP | 60-66152 | 4/1985 |
| JP | 2000-55863 | 2/2000 |
| JP | 2002-39990 | 2/2002 |
| JP | 2008-145123 | 6/2008 |

OTHER PUBLICATIONS

Decision to Grant a Patent in connection with JP 2011-531978, mailed Jun. 5, 2012, 1 page, Japanese Patent Office, Japan.
English translation of patentable claims of JP 2011-531978, 2 pages.

(Continued)

*Primary Examiner* — Alex Noguerola
(74) *Attorney, Agent, or Firm* — Antonelli, Terry, Stout & Kraus, LLP.

(57) ABSTRACT

A wet flow-type ion selective electrode device requires not only a large amount of test solution but also cumbersome management works such as flow path cleaning and device conditioning. Provided is an ion selective electrode cartridge which includes at least one ion selective electrode forming an electrical path with a reference electrode when a test solution is infused, and in which the ion selective electrode and the reference electrode is arranged to surround a container.

15 Claims, 6 Drawing Sheets

(56) References Cited

OTHER PUBLICATIONS

Communication mailed Jul. 30, 2012, in connection with European Patent Application No. 10817281.8, 3 pages, European Patent Office, Munich Germany.

Communication mailed Dec. 9, 2013, in connection with European Application No. 10817281.8; 9 pages; European Patent Office; Munich, Germany.

M. Vazquez et al.; Small-volume radial flow cell for all-solid-state ion-selective electrodes; Talanta, 62, 2004, pp. 57-63.

* cited by examiner

FIG. 6

|  | For Na ion | For K ion | For Cl ion | Reference electrode |
|---|---|---|---|---|
| Matrix material | Bis(12-crown-4) 3 wt% | Valinomicin 1.5 wt% | TODA 15wt% | KCl 60 wt% |
| Ion sensing material or a reference material | PVC 31wt% | PVC 30 wt% | PVC 42wt% | PVC 30wt% |
| Plasticizer | DOA 66wt% | DOA 68wt% | n-TDA 28wt% | DOA 10wt% |
|  |  | K-TCPB 0.03wt% | Tri-DA 5 wt% |  |
|  |  |  | NPOE 10 wt% |  |
| Solvent | THF 0.5 mL | THF 0.5 mL | THF 0.7 mL | THF 0.5 mL |

PVC: Polyvinyl chloride, DOA:                    , K-TCPB:              ,
TODA: Tetraoctylammonium brimide, n-TDA: 1-tetradecanol,
Tri-DA: Tridecyl alcohol, NPOE: O-nitrophenyl octyl ether,
THF: Tetrahydrofuran

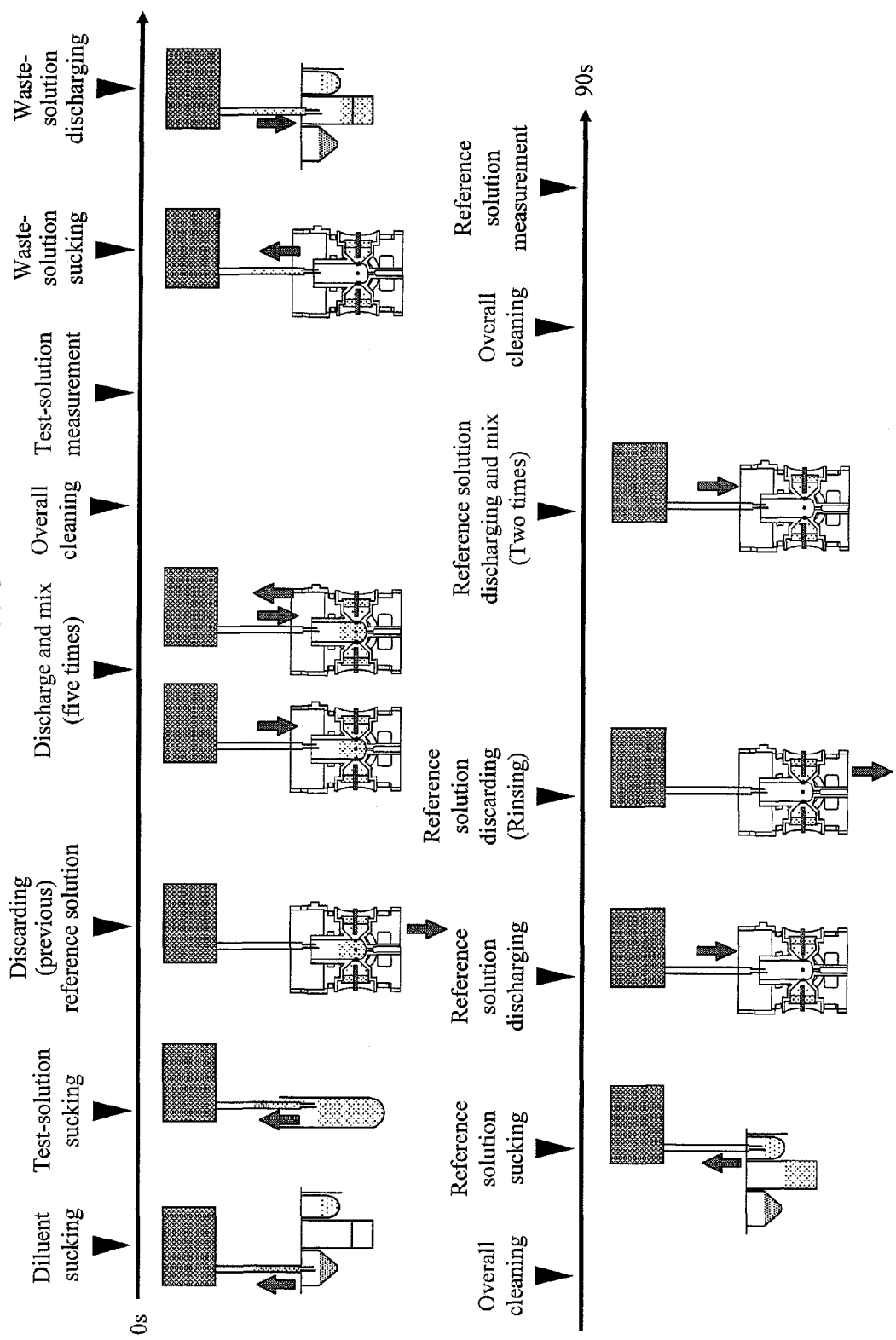

ION SELECTIVE ELECTRODE CARTRIDGE

TECHNICAL FIELD

The present invention relates to an ion selective electrode cartridge including an ion selective electrode for measuring a concentration of particular ions in a test solution.

BACKGROUND ART

Conventionally, ion selective electrodes have been used for measuring concentrations (or activities) of particular species of ions in a test solution, for example, for measuring concentrations (or activities) of particular species of ions such as Na ions, K ions, and Cl ions in a test solution such as serum used in a test room or the like in a hospital. Measurement using the ion selective electrodes includes a wet method and a dry method. For the wet method, a flow-type ion selective electrode device is generally used. In the flow-type ion selective electrode device, an ion selective electrode using an ion sensing film sensitive to particular ions and a reference electrode using a reference electrode film such as a silver/silver chloride (Ag/AgCl) electrode are provided in a flow path through which a test solution (sample) flows. The flow-type ion selective electrode device measures a potential difference (electromotive force difference) generated between the ion selective electrode and the reference electrode, and thereby measures the concentration of the particular ions in the test solution (for example, see Patent Document 1 and Patent Document 2). For the dry method, a method using an ion selective electrode in a film form has been proposed (for example, see Patent Document 3).

PRIOR ART DOCUMENTS

Patent Documents

PATENT DOCUMENT 1: Japanese Patent Application Publication No. 2008-145123
PATENT DOCUMENT 2: Japanese Patent Application Publication No. 2000-055863
PATENT DOCUMENT 3: Japanese Patent Application Publication No. 2002-039990

SUMMARY OF THE INVENTION

Problems to be Solved by the Invention

However, in spite of an advantage that a stable measurement result is easily obtained, the wet flow-type ion selective electrode device requires a large amount of test solution, and is recommended to receive regular maintenance by a service staff because of cumbersome management works such as flow path cleaning, and device conditioning. In addition, mechanisms for cleaning the flow path and for flowing out the test solution are required. Thus, downsizing of an automatic ion concentration analyzer is considered difficult.

Moreover, although the dry method is simpler and requires a smaller amount of test solution than the flow type does, it is pointed out that the dry method obtains a measurement result that has low correlation with a measurement result obtained by the wet automatic analyzer.

Hence, an object of the present invention is to provide a wet ion selective electrode cartridge achieving an automatic ion concentration analyzer that uses a smaller amount of test solution and is smaller in size and less burdened in maintenance than a conventional wet device.

Means for Solving the Problems

As the result of earnest studies, the inventors of the present invention have found that the aforementioned problems can be solved by so-called a dip-type ion selective electrode cartridge in which a container to receive a test solution infused therein is provided and in which an ion selective electrode and a reference electrode are arranged in such a manner as to surround the container, and thus have come to make the present invention.

That is, the present invention provides an ion selective electrode cartridge in which an ion selective electrode for measuring the concentration of particular ions in a test solution is arranged, the ion selective electrode cartridge including at least one ion selective electrode which forms an electrical circuit with a reference electrode when the test solution is infused in a container, the ion selective electrode cartridge being one in which each of the ion selective electrode and the reference electrode is arranged in such a manner as to surround the container.

Effects of the Invention

According to the present invention, a flow path through which a test solution is flown is not required, and thus an amount of the test solution can be reduced. With the use of the ion selective electrode cartridge, an automatic ion concentration analyzer maintenance of which is less burdened and which is small can be achieved.

BRIEF DESCRIPTION OF THE DRAWINGS

FIG. 6 is a chart showing composition examples of electrode films.
FIG. 8 is a diagram for explaining an operation example of ion concentration measurement using the ion selective electrode cartridge.

MODES FOR CARRYING OUT THE INVENTION (Ion Selective Electrode Cartridge)
An ion selective cartridge of the present invention will be described in detail by using the drawings. FIG. 1 schematically shows a configuration example of an ion selective electrode cartridge 101 to be used in an embodiment. FIG. 2 and FIG. 3 show a vertical cross-sectional structure and a horizontal cross-sectional structure of the ion selective electrode cartridge 101, respectively. The ion selective electrode cartridge 101 of the present invention includes: a container 103 into which a test solution is infused; and a reference electrode 109 and at least one ion selective electrode 110 which are arranged in such a manner as to surround the container 103.

Figure 1:
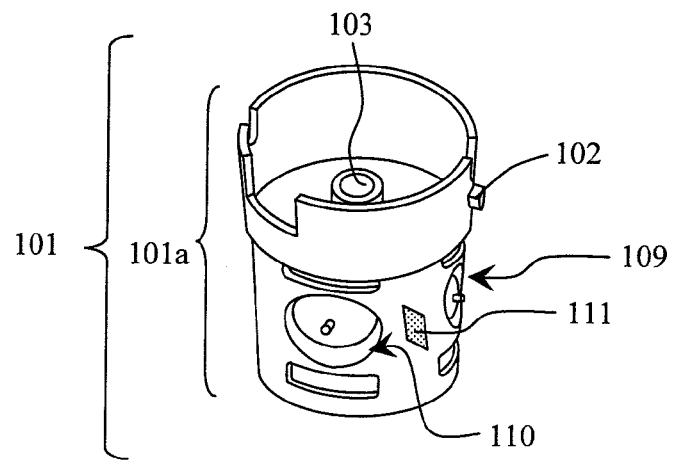
FIG. 1 is a diagram showing a schematic configuration example of an ion selective electrode cartridge.
Figure 2:
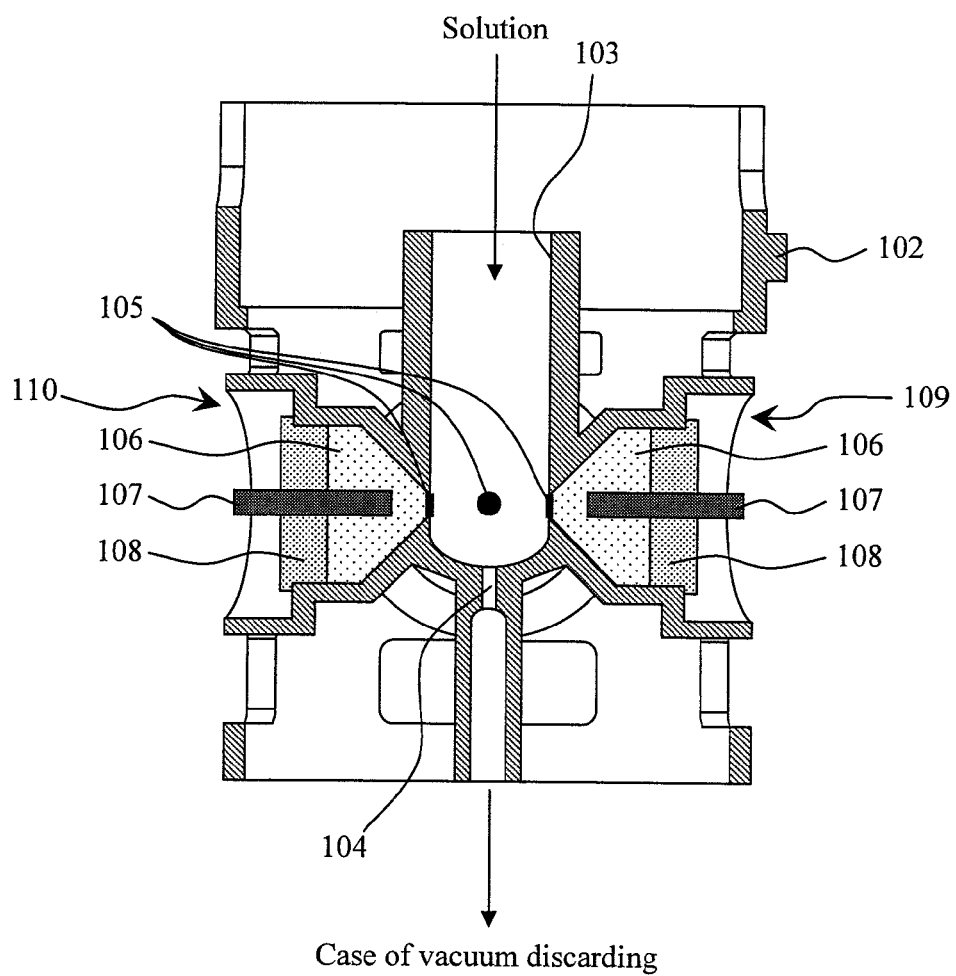
FIG. 2 is a diagram showing a vertical cross sectional structure of the ion selective electrode cartridge.
Figure 3:
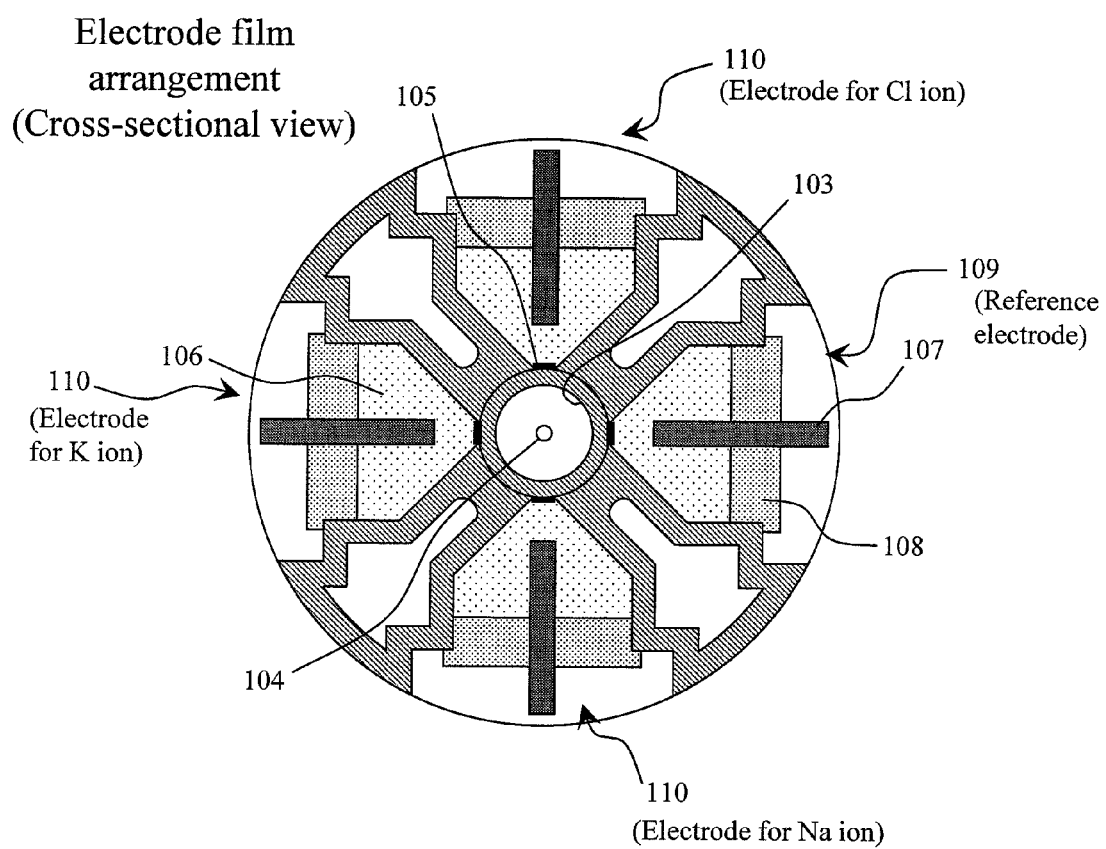
FIG. 3 is a diagram showing a horizontal cross sectional structure of the ion selective electrode cartridge.

Note that FIG. 1 to FIG. 3 show an exemplary structure in which three ion selective electrodes are arranged, and the concentrations of sodium ions (Na$^+$), potassium ions (K$^+$), and chloride ions (Cl$^-$), for example, which are particular ions in the test solution can be measured simultaneously. In addition, for example, calcium ions (Ca$^{2+}$), magnesium ions (Mg$^{2+}$), bicarbonate ions (HCO$_3^-$), lithium ions (Li$^+$), zinc ions (Zn$^{2+}$), copper ions (Cu$^{2+}$), iron ions (Fe$^{2+}$, Fe$^{3+}$), and the like can also be measured.

As a cross-sectional structure, FIG. 3 shows an example in which a casing 101a of the ion selective electrode cartridge having a substantially cylindrical shape includes the container 103 having a test tube shape and formed in such a manner as to extend along the center axis of the ion selective electrode cartridge 101, and in which the three ion selective electrode 110 and the single reference electrode 109 are arranged along an outer circumference of the casing 101a at 90 degrees intervals. As described above, it is preferable that the container 103 into which the test solution is infused be arranged in the center of the casing 101a of the ion selective electrode cartridge and that the ion selective electrodes 110 and the reference electrode 109 be arranged on a concentric circle with respect to the center of the container 103 at regular intervals. Note that it is preferable that two or more ion selective electrodes 110 be provided from a viewpoint of simultaneous measurements of multiple particular ion concentrations and that each of the reference electrode 109 and the ion selective electrodes 110 be arranged evenly on the concentric circle with respect to the center of the container 103. Incidentally, each of the reference electrode 109 and the ion selective electrodes 110 is preferably arranged on the same plane, but may be arranged at a position offset along the center axis of the casing 101a.

Figure 4:
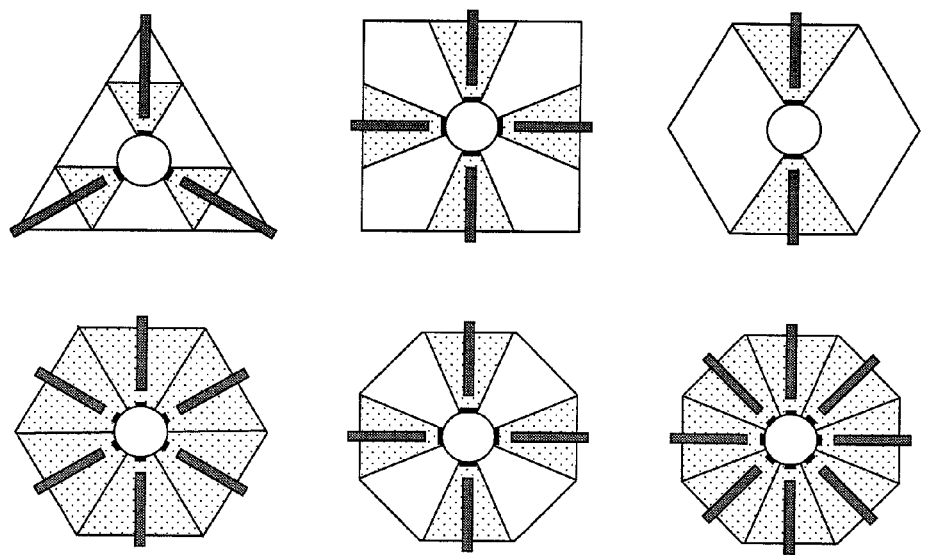
FIG. 4 is a diagram showing examples of other shapes of a casing forming the ion selective electrode cartridge.

FIG. 1 to FIG. 3 show the cylindrical casing 101a of the ion selective electrode cartridge, but the casing 101a may have a polygonal columnar shape such as a triangle columnar shape, a square columnar (rectangular parallel piped) shape, a hexagonal columnar shape, or a octagonal columnar shape, as shown in FIG. 4. Alternatively, the casing 101a may have a card shape.

It is preferable that the container 103 into which the test solution is infused have a mortar-shaped bottom portion from a viewpoint of efficient cleaning. The inclination angle of the mortar shape is preferably 90 degrees to 135 degrees, more preferably is 95 degrees to 120 degrees, and even more preferably is 100 degrees to 110 degrees. In the embodiment the container 103 having a mortar-shaped bottom portion having an inclination angle of 105 degrees is used.

Moreover, the container 103 preferably includes a discharge hole 104 in the bottom portion thereof also from the efficient cleaning viewpoint. Further, the discharge hole 104 may also be configured to allow a vacuum system or the like for suction removal to be coupled to the container 103 so that the test solution or the reference solution which are infused in the container 103 can be discharged forcedly. In this case, an appropriate diameter of the discharge hole 104 can be set in consideration of the efficiency of the solution removal.

It is preferable that the ion selective cartridge 101 of the present invention further include a positioning mechanism 102 for the reference electrode 109.

The positional relationship between each ion selective electrode 110 and the reference electrode 109 is preferably set in advance. In the structure example in FIG. 3, the ion selective electrode 110 for sodium ions (Na$^+$), the ion selective electrode 110 for potassium ions (K$^+$), and the ion selective electrode 110 for chloride ions (Cl$^-$) are arranged in this order clockwise from the reference electrode 109 as a base point, for example.

Accurate ion concentration measurement requires identification of a position at which the reference electrode 109 is attached. Hence, this embodiment employs the positioning mechanism 102 so that attaching the reference electrode 109 arranged on the casing 101a of the ion selective electrode cartridge can always be performed in only a particular positional relationship with the automatic ion concentration analyzer. Specifically, the positioning mechanism 102 having a protrusion shape for identifying the position of the reference electrode 109 is formed on the casing 101a. In addition, a guide serving as a positioning mechanism paired with the positioning mechanism 102 is formed on an inner wall surface of an attaching portion of the automatic ion concentration analyzer so that the ion selective electrode cartridge 101 can be attached to the attaching portion only when the protruding positioning mechanism 102 formed on the ion selective electrode cartridge 101 is oriented in a particular direction.

The ion selective electrode cartridge 101 of the present invention employs a structure allowing the ion selective electrode cartridge 101 to be easily attached to and detached from the automatic ion concentration analyzer, and is preferably used for measuring the concentrations of the particular ions within a range of a set working life repeatedly. For the repeated use, the ion selective electrode cartridge 101 is preferably provided with a storage means for storing how many times (how long) the ion selective electrode cartridge 101 can be used and how many times the ion selective electrode cartridge 101 is used (or the use start date and time). For example, an IC tag 111 is attached to the casing 101a as shown in FIG. 1. The IC tag 111 stores therein how many times (or how long) the ion selective electrode cartridge 101 can be used and how many times the ion selective electrode cartridge 101 is used (or the use start date and time). The IC tag 111 may further store electrode slope values Slope respectively specific to the ion selective electrodes 110 and the reference electrode 109. In the case of the multiple ion selective electrodes 110, the electrode slope values Slope are stored for each type of the ion selective electrodes 110 for the corresponding species of particular ions. For example, the electrode slope values Slope for three species of sodium ions (Na$^+$), potassium ions (K$^+$), and chloride ions (Cl$^-$) are stored.

Figure 5:
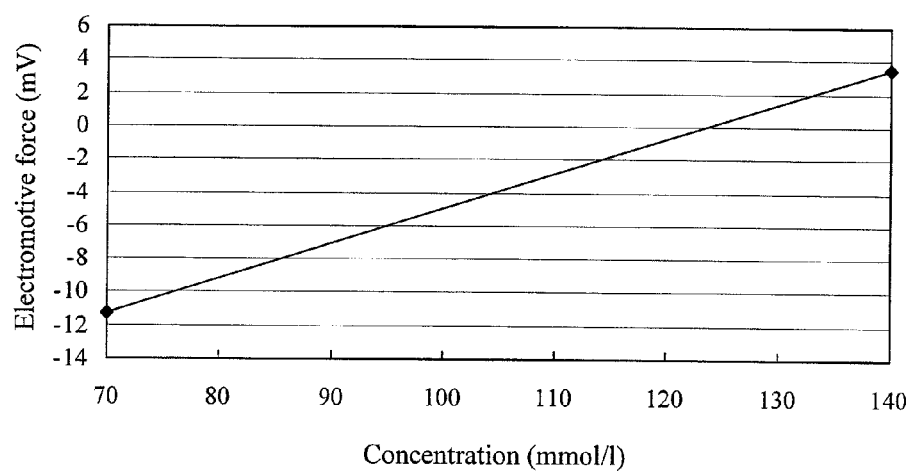
FIG. 5 is a graph showing an example of electrode slope value measurement.

Meanwhile, each of the electrode slope values Slope stored in the storage means such as the IC tag 111 is a slope representing a correspondence between an ion concentration and electrode output, that is, a slope of a relational expression (a linear equation) between the ion concentration and an electromotive force, and is obtained in advance by using the following method, for example. FIG. 5 shows a measurement example of the electrode slope value Slope of sodium ions (Na$^+$). The horizontal axis in FIG. 5 represents a concentration, and the vertical axis represents an electromotive force. Each ion selective electrode 110 necessarily has an individual difference. Thus, the following steps are performed before the ion selective electrode cartridge 101 is shipped as a product. Specifically, electromotive forces $E_H$ and $E_L$ each generated between a reference electrode 109 and the ion selective electrode 110 are measured respectively for a high-concentration reference solution $C_H$ and a low-concentration reference solution $C_L$. Then, an electrode slope value Slope of an internal electrode to be used for particular ion concentration measurement is calculated based on the following formula.

$$\text{Slope} = (E_H - E_L) / \text{Log}(C_H / C_L) \qquad \text{(Formula 1)}$$

Note that the above formula can be derived from the Nernst equation.

Next, a description is given of electrode structures of the reference electrode 109 and the ion selective electrode 110. Small holes are formed in an inner surface of the container 103 every 90 degrees in a circumferential direction of the container 103. Each of the small holes, however, is closed by an electrode film 105 allowing only a particular ion to be measured to pass therethrough. FIG. 6 shows an example of a compound composition of each electrode film 105. Employing the electrode film 105 having the corresponding compound composition shown in FIG. 6 makes it possible to achieve a long life of the ion selective electrode cartridge 101. For example, the need for replacing the ion selective electrode cartridge 101 can be eliminated in 150 samples or more or for one month or longer. As the result of long-time stableness of the characteristic of the electrode film 105, the ion selective electrode cartridge 101 can be handled with the electrode slope value Slope considered to be constant during the use of the ion selective electrode cartridge 101. In an example, the necessity for a calibration of the electrode slope value Slope every measurement can be eliminated.

Further, spaces to be filled with an inner gel 106 outside the electrode films 105 are prepared in the casing 101a. A gel obtained by mixing an electrolyte solution (an aqueous solution) including a conductive material such as sodium chloride of 10 mmol/L, for example, and CMC (3 wt % of carboxymethyl cellulose) together is used as the inner gel 106. Each of the spaces filled with the inner gel 106 is closed with a cap 108 having an internal electrode 107. Note that a silver wire of 1 mm in diameter is used for the internal electrode 107. Incidentally, an end portion of the internal electrode 107 is plated with a hydrochloric acid solution to form silver chloride AgCl. The electrode films 105, the inner gel 106, and the caps 108 each having the internal electrode 107 form the ion selective electrodes 110 and the reference electrode 109 which are described above.

Figure 7:
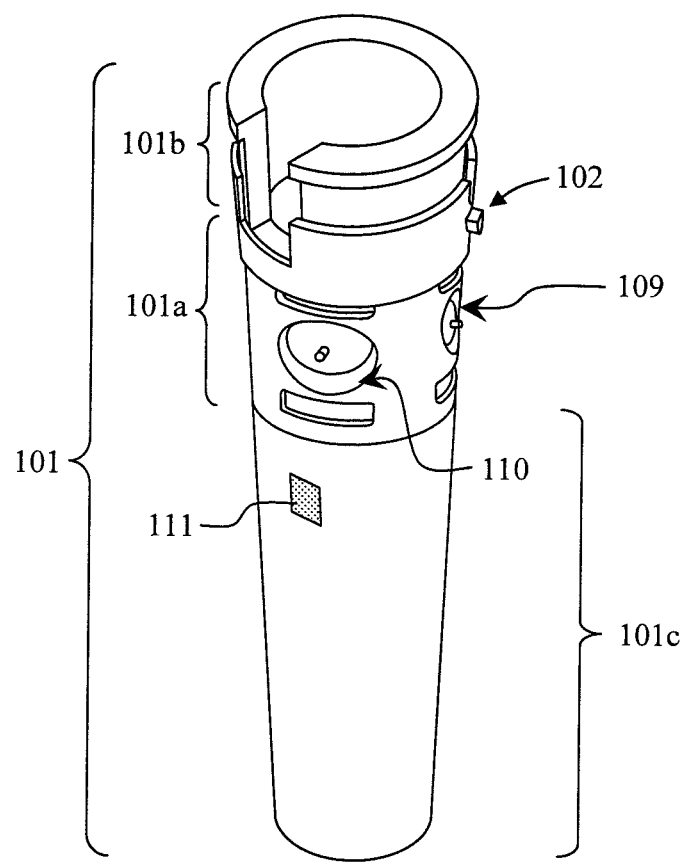
FIG. 7 is a diagram showing an example of use mode of the ion selective electrode cartridge.

The ion selective electrode cartridge 101 of the present invention may further include a guide unit 101b or a waste solution tank 101c as shown in FIG. 7. The guide unit 101b is a member which serves as a guide when the ion selective electrode cartridge 101 is attached to the automatic ion concentration analyzer, and is exposed from a surface of the analyzer in the attached state to facilitate attaching and detaching. A cut-out is preferably provided in a circumference of the guide unit 101b as shown in FIG. 7 so as not to hinder movement of a probe for infusing the test solution and the reference solution into the container 103 (that is, in only one portion of a side surface over which the probe moves). The waste solution tank 101c is a container for collecting a waste solution which is attached on the lower surface side of the casing 101a. The aforementioned IC tag 111 may be attached to the waste solution tank 101c as shown in FIG. 7. In consideration of environmental pollution, the reference solution is assumed to be main waste solution. A waste test solution is preferably collected in a reagent cartridge or the like and then treated as a biohazard. Alternatively, it is also possible to collect all the waste test solutions in the waste solution tank 101c and then to treat the waste solution tank 101c as a biohazard. In this case, what is required is to discard only the waste solution tank 101c, which has an effect that garbage amount is reduced in a test site. In this embodiment, all the waste reference solutions resulting within the guaranteed use times or use period are collected in the waste solution tank 101c. A structure can also be employed in which the waste solution tank 101c is connected with a waste solution tank receiving a waste solution flowing from a cleaning station of the automatic ion concentration analyzer.

(Method of Manufacturing Ion Selective Electrode Cartridge)

A method of manufacturing the ion selective electrode cartridge 101 of the present invention, which is not particularly limited, is manufactured as follows, for example.

Firstly, a casing 101a including a container 103 having two or more holes for electrode film formation and spaces to be filled with electrolyte solutions outside the holes for electrode film formation is prepared. The holes are provided in such a manner that the at least one ion selective electrode 110 and the reference electrode 109 can be formed to surround the container 103 into which the test solution is infused. Polyvinyl chloride is particularly preferable as the material of the casing 101a. A material of the casing 101a is not particularly limited, but polyvinyl chloride, polypropylene, polystylene, polycarbonate, and the like are cited as the material from a viewpoint of easy treatment and handling. Preferably, the material is polyvinyl chloride. Next, electrode films 105 are formed on the holes for electrode film formation in the container 103 into which the test solution is infused. Each of the electrode films 105 is formed by casting a solution into the corresponding hole for electrode film formation, the solution being obtained by mixing a matrix material of a high polymer material such as polyvinyl chloride, either an ion sensing material or a reference material, and a plasticizer together in an appropriate solvent. Specifically, the solution obtained by mixing the matrix material, either the ion sensing material or the reference material, and the plasticizer together in the appropriate solvent is firstly cooled to −5 degrees C. Thereafter, the mixed solution is cast into the holes for electrode film formation without being kept at the temperature. Note that the electrode films are desirably formed at a temperature of 6 degrees C. to 8 degrees C. and at a humidity of 70% or lower in consideration of post-manufacturing stability of the films. The temperature and the humidity of the atmosphere are preferably maintained at the aforementioned ranges particularly until the cast solution is dried to form the films. In addition, the manufacturing is performed, while the temperature of the container 103 is maintained at 6 degrees C. to 8 degrees C., and after it is checked that a difference between the outer air temperature and the temperature of the container 103 is within 1 degree C.

Further, a test can be performed after resistances of the electrode films are measured in manufacturing the films. For example, each space provided outside the corresponding hole for electrode film formation and the container 103 are filled with an electrolyte solution containing a conductive material such as sodium chloride of 10 mmol/L. At this time, the other holes are temporarily closed or filled with the same conductive material. Suppose a case where the corresponding electric resistance is measured through the conductive material. If each film is formed, a resistance value of 2 Megaohms or higher is shown in a case of sodium chloride of 17 mmol/L, for example. On the other hand, if the film is not formed (is broken), resistance of 500 Kiloohms or lower is shown. As described above, performing the tests of intermediate products enables reduction of a proportion defective. Next, in the intermediate products passing the test, the spaces provided outside the holes for electrode film formation are filled with an electrolyte solution containing the conductive material such as sodium chloride of 10 mmol/L. Note that the electrolyte solution is preferably in a gel state from a viewpoint of less likeliness of evaporation and excellent handling. Next, caps 108 each including an internal electrode 107 at the center thereof are prepared, the internal electrode 107 having an end formed of silver/silver chloride. Each cap 108 is fixed in such a manner as to close the corresponding space so that the internal electrode 107 can be soaked in the electrolyte solution, so that the electrolyte solution is confined in the space. At this time, the electrode is preferably fixed using thermocompression bonding, ultrasonic compression bonding, an adhesive, or the like.

(Measurement Targets)

Examples of the particular ions suitable for the measurement using the ion selective electrode cartridge of the present invention include sodium ions ($Na^+$), potassium ions ($K^+$), chloride ions ($Cl^-$), calcium ions ($Ca^{2+}$), magnesium ions ($Mg^{2+}$), bicarbonate ions ($HCO_3^-$), lithium ions ($Li^+$), zinc ions ($Zn^{2+}$), copper ions ($Cu^{2+}$), iron ions ($Fe^{2+}$, $Fe^{3+}$), and the like. Examples of the test solution include a solution derived from any of blood, urine, soil, and water, and the like.

(Operation of Measuring Ion Concentrations)

Next, an example of an operation of measuring ion concentrations using the ion selective electrode cartridge of the present invention will be described by using FIG. 9. Normally, the ion concentrations are herein measured automatically by an automatic ion concentration analyzer.

The ion selective electrode cartridge 101 is attached to the automatic ion concentration analyzer at a predetermined position before the ion concentration measurement. Note that the ion selective electrode cartridge 101 is used for the ion concentration measurement without replacement work within usable times as a working life or a usable period. Further, as work before the start of the ion concentration measurement, containers into which a test solution, a diluent, and a reference solution are dispensed are set at predetermined positions of the automatic ion concentration analyzer.

After the end of the preparation work, a diluent sucking step is started. A probe is positioned in a container containing the dispensed diluent, and the diluent is sucked into the probe.

Subsequently, a test-solution sucking step is executed. The probe is positioned in a container containing the dispensed test solution, and the test solution is additionally sucked into the probe. It is preferable to suck air in advance before sucking the test solution. Sucking air in advance can lead to avoidance of a situation where liquid surfaces of the diluent and the test solution are in direct contact with each other.

Next, the process moves to a step of discarding a reference solution remaining in the ion selective electrode cartridge 101 from the previous measurement. In this step, a vacuum system or the like is activated, which causes a state where the air pressure is lower outside at a bottom portion of the container 103 than in the inside thereof. This air pressure difference (so-called vacuum drawing) causes the reference solution remaining from the previous measurement in the container 103 to be discharged to the waste solution tank 101c through the discharge hole 104.

After the end of the reference-solution discarding step, the treatment process moves to a test-solution diluting step. At this time, the probe is positioned at a position at which the ion selective electrode cartridge 101 is attached. Subsequently, the probe is driven downward until a tip end thereof reaches the inside of the container 103 of the ion selective electrode cartridge. Thereafter, the test solution and the diluent are discharged from the probe into the container 103. At this time, the sucking and discharging a mixed solution (diluted test solution) are repeated certain times by using the probe to mix the test solution and the diluent together well in the container 103. Then, the tip end of the probe is drawn back from the mixed solution.

Next, a probe cleaning step is executed. The probe is moved up to a position of a cleaning station provided to the automatic ion concentration analyzer. In the cleaning step, both an outer wall surface of the probe and the inside thereof are cleaned with purified water. A waste solution in this step contains components of the test solution, but an amount of the test solution with respect to the purified water is extremely small. There is no concern about environmental pollution.

After the end of or in such a manner as to be parallel with the cleaning step, measurement of concentrations of ions contained in the mixed solution is started. Note that the ion concentration measurement is preferably started a predetermined time (for example, 30 seconds) after the end of an operation of stirring the mixed solution. This is because ion concentration measurement values are not stable immediately after the end of the stirring operation in some cases. Note that when multiple ion selective electrodes 110 are formed in the ion selective electrode cartridge 101, the ion concentration measurement is executed for each ion selective electrode 110.

For example, an electromotive force appearing between the internal electrode 107 of the reference electrode 109 and the internal electrode 107 of each ion selective electrode 110 for sodium ions (Na+), potassium ions (K+), or chloride ions ($Cl^-$) is measured. When the multiple ion concentrations are measured as described above, the measurements may be performed in turn, but it is preferable that all the electromotive forces be simultaneously measured in consideration of a variation or the like of a measurement environment.

It is desirable that each measurement of the corresponding electromotive force be repeated multiple times and that an average value thereof be used as a measurement result. For example, six electromotive force measurements are executed for each ion species, and an average value of values not including the maximum value and the minimum value is used as a measurement result. The measurement result is held until a measurement result of the reference solution to be described later is obtained.

After the end of the test-solution measuring step, the process moves to a waste-solution sucking step. In this step, the probe is driven downward until the tip end thereof reaches the inside of the container 103 of the ion selective electrode cartridge. Then, all of the mixed solution (diluted test solution) in the container 103 is sucked into the probe.

When the sucking of the mixed solution (diluted test solution) is completed, the probe is drawn back, and then is driven to a solution discarding position. Thereafter, the mixed solution (diluted test solution) is discharged from the probe to the discarding tank to be discarded thereinto. Note that the test solution having the possibility of a biohazard is discarded into a sealed discarding tank (for example, a reagent cartridge).

After the end of the discarding of the mixed solution used for the measurement, the probe cleaning step is started. At this time, the probe is moved up to the position of the cleaning station provided to the automatic ion concentration analyzer. Also in the cleaning step, both the outer wall surface of the probe and the inside thereof are cleaned with purified water. A waste solution also contains components of the test solution, but an amount of the test solution with respect to the purified water is extremely small. There is no concern about environmental pollution.

Next, an ion-concentration measurement step using the reference solution (that is, an ion-concentration measurement-value calibration step) is started. At this time, the probe is positioned at the position at which the container containing the dispensed reference solution is attached, so that the reference solution is sucked into the probe.

Subsequently, the process moves to a first reference-solution discharging step. At this time, the probe is positioned at the position at which the ion selective electrode cartridge 101 is attached. Next, the probe is driven downward until the tip end thereof reaches the inside of the container 103 of the ion selective electrode cartridge 101. Thereafter, some of the reference solution is discharged from the probe into the container 103. The reference solution is used to rinse the container 103 contaminated with the test solution. When a predetermined amount of the reference solution is dispensed in the container 103, the vacuum system or the like is activated, which causes the state where the air pressure is lower outside the bottom portion of the container 103 than in the inside thereof. This air pressure difference (so-called vacuum drawing) causes the reference solution dispensed into the container 103 to be discharged to the waste solution tank 101c through the discharge hole 104. The waste reference solution also contains components of the test solution, but an amount of the test solution is extremely small. There is no concern about environmental pollution.

After the end of the discarding step (rising step), the reference solution left in the probe is discharged into the container 103. That is, a second reference-solution discharging step is executed. At this time, there is a slight temperature difference between the very small amount of reference solution left in the container 103 and the reference solution in the probe. Sucking and discharging the reference solution are repeated certain times by using the probe to eliminate the temperature difference.

Thereafter, the tip end of the probe is withdrawn upward from the container 103. Note that the ion concentration measurement of the reference solution is started a predetermined time (for example, 30 seconds) after the end of an operation of stirring the reference solution. This is because ion concentration measurement values are not stable immediately after the end of the stirring operation in some cases.

The time period is utilized to execute a probe cleaning step. At this time, the probe is moved up to the position of the cleaning station. Also in the cleaning step, both the outer wall surface of the probe and the inside thereof are cleaned with purified water. After the completion of the cleaning, the probe is withdrawn to an initial position.

After the elapse of the predetermined time from the end of the reference solution stirring, the ion concentration measurement of the reference solution is started. When the multiple ion selective electrodes 110 are formed in the ion selective electrode cartridge 101, the ion concentration measurement is executed for each ion selective electrode 110.

For example, an electromotive force appearing between the internal electrode 107 of the reference electrode 109 and the internal electrode 107 of each corresponding ion selective electrode 110 for sodium ions (Na+), potassium ions (K+), or chloride ions (Cl⁻) is preferably measured at the same time.

Each electromotive force measurement is executed under the same condition as that for the measurement of the test solution. Thus, it is desirable that each measurement of the corresponding electromotive force be repeated multiple times and that an average value thereof be used as a measurement result. For example, six electromotive force measurements are executed for each ion species, and an average value of values not including the maximum value and the minimum value is used as a measurement result.

The operation described above results in all the measurement values required to calculate the ion concentrations in the test solution. Subsequently, the automatic ion concentration analyzer calculates each concentration value of the particular ions in the test solution based on: the electromotive force measured for the particular ions in the test solution; the electromotive force measured for the particular ions in the reference solution; and the electrode slope value Slope specific to the ion selective electrode 110 used for the measurement. Specifically, in order to correct an error due to so-called an intercept variation due to occurrence of a drift of the electrode electromotive force, the concentration value of the particular ions existing in the test solution is calculated from: the electromotive force measured for the particular ions in the reference solution; the electromotive force measured for the particular ions in the test solution; and the electrode Slope value held by the ion selective electrode 110 used for the measurement.

Thus, the operation of measuring the particular ions in the single test solution is completed. The same measurement operation is also executed for a different test solution, as necessary.

(Conclusion)

As described above, the ion selective electrode cartridge 101 in which the one or more ion selective electrodes 110 and the reference electrode 109 are arranged at regular intervals around the container 103 centered therein is employed, and thereby the necessity for the flow path through which the test solution flows can be eliminated despite the wet-type method. Thus, there is no concern about solution leakage, and the burden on maintenance is reduced. In addition, since the necessity for the flow path is eliminated, a required solution amount of the test solution can be reduced. Consequently, making the automatic ion concentration analyzer smaller can be achieved. Moreover, with the employment of this structure, both the design and casing strength of the casing 101a can be achieved.

Besides, the ion selective electrode cartridge 101 according to the embodiment can be used repeatedly for the ion concentration measurement within the preset working life of the ion selective electrode cartridge 101. Thus, it is possible to reduce labor and costs required to replace the ion selective electrode cartridge 101 for each test solution.

Further, providing the positioning mechanism 102 to the ion selective electrode cartridge 101 makes it possible to identify the position at which the reference electrode 109 is attached with respect to the automatic ion concentration analyzer. This can guarantee the correspondence between each ion selective electrode 110 used for particular ion concentration measurement and the corresponding electrode slope value Slope specific to the internal electrode 107 of the ion selective electrode 110. Employing this mechanism can enhance the reliability of the calculated ion concentration.

Still further, when the discharge hole 104 allowing the solution to be discarded due to the vacuum drawing is arranged in the bottom portion of the container 103 of the ion selective electrode cartridge 101, a solution not having a possibility of biohazard can be immediately discarded without the need for driving the probe and other movable portions. Thereby, a time required to measure the ion concentration of a single test solution can be made shorter.

(Other Embodiment)

Hereinbelow, a description is given of a modification of the embodiment described above.

(Other Composition Example of Electrode Film)

In the aforementioned description, the case where the electrode films are formed in the compositions shown in FIG. 7 has been described. Meanwhile, an electrode film in a composition shown below may be used for the electrode film for the chloride ions, instead of the composition shown in FIG. 7. In other words, an electrode film 105 formed in the following manner may be used for the chloride ions. Specifically, weighing and addition are performed in percentages that polyvinyl chloride (PVC) as a chloride sensing material is 19% by weight, 1-tetradecanol (n-TDA) as a first plasticizer is 24% by weight, o-nitrophenyl octyl ether (o-NPOE) as a second plasticizer is 10% by weight, tridecyl alcohol (nTriDA) as a third plasticizer is 5% by weight, and a high polymar material (TODA) as a matrix material is 42% by weight, and then tetrahydrofuran is added to the solution for dispersion, so that the electrode film 105 is formed.

The following shows a specific example of measurement results of measurement performed using a control serum (Seronorm (registered trademark) Human produced by SERO AS and imported by SEKISUI MEDICAL Co., Ltd.) by using an ion selective electrode cartridge manufactured while the new composition is applied to an electrode film for the chloride ions. Note that, the ion selective electrode cartridge includes three electrodes formed therein, the electrodes including a Na electrode and a K electrode in addition to the Cl electrode. In addition, concentrations as the measurement results are obtained through the aforementioned real-time calculations of the electrode slope values Slope.

Table 1 shows relationships between the measurement results measured by an automatic analyzer and electrode slope values Slope. Note that a reference solution in Table 1 corresponds to the high-concentration reference solution CH, and a ⅔ reference solution corresponds to the low-concentration reference solution CL.

TABLE 1

|  | Na | K | Cl |
|---|---|---|---|
| Potential at specimen (mV) | 35.981 | 61.037 | 58.450 |
| Potential in reference solution(mV) | 34.474 | 67.050 | 63.623 |
| Potential in ⅔ reference solution (mV) | 24.842 | 56.451 | 72.954 |
| Electrode slope value calculated during measurement (actual slope value) | 55 | 55 | −52 |
| Initial slope value | 56 | 57 | −50 |
| Slope value criteria | 40 to 70 | 40 to 70 | −40 to −70 |
| Concentration (mmol/L) (case of calculation using initial value as slope value) | 149.0 | 3.92 | 125.7 |
| Concentration (mmol/L) (case of calculation using actual slope value) | 149.2 | 3.89 | 124.7 |
| Measurement value for reference (mmol/L) | 147 ± 4 | 3.7 ± 0.2 | 121 ± 4 |

EXPLANATION OF THE REFERENCE NUMERALS

101 . . . ion selective electrode cartridge, 101a . . . casing, 101b . . . guide unit, 101c . . . waste solution tank, 102 . . . positioning mechanism, 103 . . . container, 104 . . . discharge hole, 105 . . . electrode film, 106 . . . inner gel, 107 . . . internal electrode, 108 . . . cap, 109 . . . reference electrode, 110 . . . ion selective electrode, 111 . . . IC tag

The invention claimed is:

1. An ion selective electrode cartridge equipped with an ion selective electrode for measuring a concentration of particular ions in a test solution, the ion selective electrode cartridge comprising:
a casing having a substantially cylindrical or polygonal columnar share and including a container into which the test solution is infused, the container extending along the center axis of the ion selective electrode cartridge;
a reference electrode; and
at least one ion selective electrode which forms an electrical path with the reference electrode when the test solution is infused, wherein the at least one ion selective electrode and the reference electrode are arranged along an outer circumference of the casing to surround the container.

2. The ion selective electrode cartridge according to claim 1, wherein
the container is arranged in the center of the casing, and
the at least one ion selective electrode and the reference electrode are arranged evenly spaced on a concentric circle around the center axis of the container.

3. The ion selective electrode cartridge according to claim 2, comprising two or more ion selective electrodes, wherein
the reference electrode and the two or more ion selective electrodes are arranged evenly spaced on the concentric circle around the center axis of the container.

4. The ion selective electrode cartridge according to claim 2, wherein the at least one ion selective electrode and the reference electrode are each arranged in the same plane.

5. The ion selective electrode cartridge according to claim 1, wherein the container comprises a bottom portion having a mortar shape.

6. The ion selective electrode cartridge according to claim 1, comprising
a discharge hole in the bottom portion of the container.

7. The ion selective electrode cartridge according to claim 1, further comprising
a positioning mechanism for the reference electrode.

8. The ion selective electrode cartridge according to claim 1, wherein
the ion selective electrode cartridge is repeatedly used for measuring a concentration of particular ions within a preset working life.

9. The ion selective electrode cartridge according to claim 1, wherein
the particular ions include one or more species of ions selected from the group of sodium ions, potassium ions, chloride ions, calcium ions, magnesium ions, bicarbonate ions, lithium ions, zinc ions, copper ions, and iron ions.

10. The ion selective electrode cartridge according to claim 1, wherein
the test solution is a solution derived from any of blood, urine, soil and water.

11. A method for manufacturing the ion selective electrode cartridge according to claim 1, the method for manufacturing the ion selective electrode cartridge comprising:
preparing a casing including container having two or ore holes for electrode formation and spaces to be filled with electrolyte solutions outside the holes for electrode formation;
forming electrode films corresponding to at least an ion selective electrode and a reference electrode over the two or more holes for electrode film formation of the ion selective electrode cartridge by
cooling mixed solutions each containing a composition material for the electrode films to a predetermined temperature at or below freezing point;
casting the mixed solutions into the two or more holes for electrode film formation; and
forming the electrode films by drying the mixed solutions after the casting in an atmosphere maintained at a temperature of 6° C. to 8° C. and at a humidity of 70% or lower.

12. The ion selective electrode cartridge according to claim 1, wherein the at least one ion selective electrode and the reference electrode are each arranged in the same plane.

13. The ion selective electrode cartridge according to claim 1, wherein the at least one ion selective electrode and the reference electrode are arranged at a position offset along the center axis of the casing.

14. The ion selective electrode cartridge according to claim 1, wherein the at least one ion selective electrode and the reference electrode are each disposed in a separate radial direction extending from the center axis of the container.

15. An ion selective electrode cartridge equipped with an ion selective electrode for measuring a concentration of particular ions in a test solution, the ion selective electrode cartridge comprising:
   a casing including a container into which the test solution is infused, the container extending along the center axis of the ion selective electrode cartridge;
   a reference electrode; and
   at least one ion selective electrode which forms an electrical path with the reference electrode when the test solution is infused, wherein
   the at least one ion selective electrode and the reference electrode are arranged along an outer circumference of the casing to surround the container.

* * * * *